United States Patent [19]
Hyman

[11] Patent Number: 4,971,903
[45] Date of Patent: Nov. 20, 1990

[54] PYROPHOSPHATE-BASED METHOD AND APPARATUS FOR SEQUENCING NUCLEIC ACIDS

[76] Inventor: Edward Hyman, Apt. 8C., 1000 Windsor Shore Dr., Columbia, S.C. 29223

[21] Appl. No.: 173,433

[22] Filed: Mar. 25, 1988

[51] Int. Cl.$^5$ .......................... C12Q 1/68; C12Q 1/66
[52] U.S. Cl. ........................................... 435/6; 435/8
[58] Field of Search ........................................ 435/6, 91

[56] References Cited

PUBLICATIONS

Sanger et al, Proc Natl Acad Sci 74(12) (1977), pp. 5463–5467.
Maxam et al, Proc Natl Acad Sci 74(2) (1977), pp. 560–564.
Wu et al., J. Molecular Biology 35, 523–37 (1968).
Donis-Keller, Nucleic Acid Research 8, 3133–3142 (1980).
Tabor et al., Proc. Nat'l. Acad. Sci. (U.S.A.) 84, 4767–4771 (1987).
Guranowski et al., J. Biol. Chem. 261, 5943–5946 (1986).
Idahl et al., Analytical Biochem. 155, 177–181 (1986).
Ugarova et al., Analytical Biochem. 158, 1–5 (1986).
DeWet et al., Proc. Nat'l. Acad. Sci. (U.S.A.) 82, 7870–7873 (1985).
Kricka et al., Analytical Biochem. 129, 392–397 (1983).
Moyer et al., Analytical Biochem. 131, 187–189 (1983).
Lundin, in Luminescent Assays: Perspectives in Endocrinology and Clinical Chemistry (Send and Pazzagli, eds) 1, 29–45 (1982).
Nicholas et al., Analytical Biochem. 114, 396–397 (1981).
Brovko et al., Biokhimiya 45, 1582–1588 (1980).
Brovko et al., Biokhimiya 43, 798–805 (1978).
Lee et al., Analytical Biochem. 80, 496–501 (1977).
Lundin et al., Analytical Biochem. 75, 611–620 (1976).
DeLuca et al., Biochemistry 13, 921–925 (1974).
Balharry et al., Analytical Biochem. 40, 1–17 (1971).
McElroy et al, Arch. Biochem. Biophysics 64, 257–271 (1956).
Nyren et al., Analytical Biochem. 151, 504–509 (1985).
Robbins et al., J. Biol. Chem. 233, 686–690 (1958).
Nicholls, Biochem. J. 165. 149–155 (1965).
Berg et al., J. Biol. Chem. 210, 657–672 (1957).
Noda, in The Enzymes (Boyer, ed).
Sawhney et al., Plant Sci. Letters 6, 103–110 (1976).
Wilson et al., J. Biol. Chem. 233, 975–981 (1958).
Darrow et al., Methods in Enzymology 5, 226–235 (1962).
Seal et al., J. Biol. Chem. 251, 975–981 (1976).
Kaguni et al., Proc. Nat'l. Acad. Sci. (U.S.A.) 80, 2221–2225 (1983).
Kunkel et al., Proc. Nat'l. Acad. Sci. (U.S.A.) 78, 6734–6738 (1981).

*Primary Examiner*—Amelia Burgess Yarbrough
*Assistant Examiner*—Scott Chambers

[57] ABSTRACT

A method for sequencing nucleic acid polymers is provided in which the polymer to be sequenced acts as a template for the production of a complementary polymer by a polymerase enzyme. The template polymer is introduced into a polymerization environment in which production of the complementary polymer will occur if appropriate nucleotides are provided. The nucleotides are then provided to the polymerization environment one at a time in individual feedstocks. If the nucleotide in a feedstock is complementary to the next base in the template polymer, i.e., the unpaired base closest to the growing end of the complementary polymer, polymerization will occur lengthening the complementary polymer and releasing PPi. By separately recovering each feedstock and analyzing it for the presence of PPi, the sequence of the complementary polymer and thus the template polymer is determined.

13 Claims, 6 Drawing Sheets

PYROPHOSPHATE-BASED METHOD AND APPARATUS FOR SEQUENCING NUCLEIC ACIDS

BACKGROUND OF THE INVENTION

This application relates to a new method for sequencing nucleic acids without the use of electrophoresis, radioactivity, or fluorescense. The technique analyzes the production of inorganic pyrophosphate from nucleic acid polymerization reactions, and has the advantages of being simple, cost effective, and completely automatable.

Current methods used to sequence nucleic acids all involve electrophoresis of single stranded nucleic acid fragments (ssDNA or ssRNA) generated by either chain terminating nucleotides in the Sanger dideoxy sequencing technique, selective enzymatic fragmentation of strands of RNA or selective chemical degradation of DNA by the Maxam and Gilbert technique. All of these methods involve separation of nucleic acid fragments in polyacrylamide gels and measurement of their location by radioactivity. New DNA sequencing machines recently made commercially available use fluorescense instead of radioactivity to detect the ssDNA fragments. However, these newer techniques involve expensive equipment, specialized chemicals, and still require intensive labor and careful technique to carry out the procedure successfully.

The present invention takes a completely different approach to the problem of sequencing nucleic acids based on the precise measurement of the inorganic pyrophosphate (PPi) generated during nucleic acid polymerization reactions, such as the polymerization of deoxynucleotide triphosphates (dNTP) with a ssDNA template—primer complex catalyzed by DNA polymerase shown below:

ssDNA—primer+dNTP→ssDNA—(-primer+dNMP)+PPi

As shown, one PPi is generated for each dNTP consumed and incorporated into the DNA. If, for example x moles of ssDNA template—primer all have their primer chains extended by one base, then x moles of PPi will be generated. If the primer chains are extended by two bases, then 2x moles of PPi will be generated, etc. Thus, by precisely measuring PPi, it is possible to determine whether or not a polymerization reaction has occurred, and if so, determine how many nucleotides have been incorporated in the growing primer chain.

Because PPi is formed in a number of biosynthetic pathways, a number of different methods have been developed to assay for PPi. One such assay uses two enzymes, ATP-sulfurylase and firefly luciferase, to produce a light emission proportional in intensity to the amount of PPi. Nyren et al., 151 *Analytical Biochemistry* 504 (1985). The reactions occurring in this assay are PPi + adenosine-5'-phosphosulfate 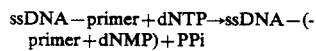 ATP + SO$_4^{2-}$ ATP + luciferin + O$_2$ →luciferase→ oxyluciferin + AMP
+PPi +CO$_2$ + hν.

The second half of this reaction scheme has also been used as an assay for ATP. Luciferase, however, is not entirely specific for ATP as a high energy substrate and can also react with deoxyadenosine-5'-triphosphate (dATP) and to a lesser extent may react with other nucleoside triphosphates as well. Moyer et al., 131 *Analytical Biochemistry* 187 (1983).

The measurement of PPi has not previously been considered as a means of determining a nucleic acid sequence. As will be shown hereinbelow, however, this approach provides a simple method for rapid determination of nucleic acid sequences.

SUMMARY OF THE INVENTION

The claimed invention provides a method for sequencing nucleic acid polymers in which the polymer to be sequenced acts as a template for the production of a complementary polymer by a polymerase enzyme. According to the invention, the template polymer is introduced into a polymerization environment in which production of the complementary polymer will occur if appropriate nucleotides are provided. The nucleotides are then provided to the polymerization environment one at a time in individual feedstocks. If the nucleotide in a feedstock is complementary to the next base in the template polymer, i.e., the unpaired base closest to the growing end of the complementary polymer, polymerization will occur lengthening the complementary polymer and releasing PPi. By separately recovering each feedstock and analyzing it for the presence of PPi, the sequence of the complementary polymer and thus the template polymer is determined.

A preferred method according to the invention utilizes ATP-sulfurylase and an ATP-dependent luciferase to analyze the recovered feedstocks for inorganic pyrophosphate. In this method, each feedstock advantageously comprises a nucleotide, APS, and luciferin. When this feedstock is provided to the polymerization environment, the nucleotide, if complementary to the next base in the template polymer, will be consumed and PPi will be generated. The recovered feedstock thus will contain PPi, APS and luciferin, a suitable mixture for generating light by the coupled reactions of ATP-sulfurylase and luciferase, if the base was complementary.

DETAILED DESCRIPTION OF THE INVENTION

Figure 1:
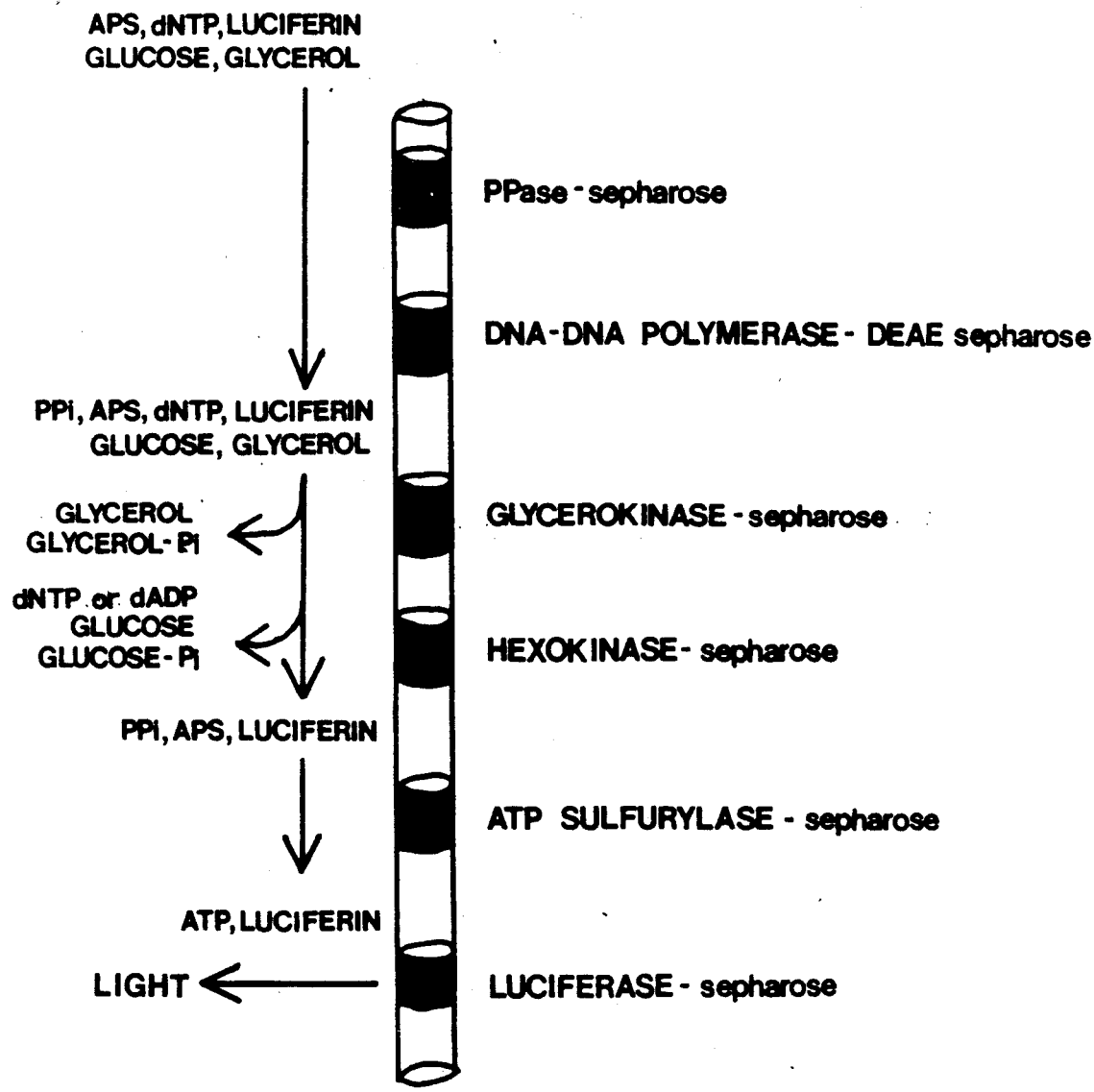
FIG. 1 shows a schematic diagram of a preferred sequencing method according to the invention.

The preferred sequencing process according to the invention is diagrammed in FIG. 1. This process involves the use of a series of precisely ordered columns each containing an enzyme covalently attached to a support such as sepharose 4B. For determination of a DNA sequence, feedstock solution containing adenosine-5'-phosphosulfate (APS), glucose, glycerol, luciferin, and one of the four dNTPs (dATP, dGTP, dCTP, or dTTP) is introduced into the first column, a pyrophosphatase column.

PPi is a common contaminant of some commercially sold chemicals like TrisOAc and is difficult to remove from the buffers on a large scale before using in the procedure. Furthermore, small nuclease contaminants in the buffers can potentially catalyze the formation of PPi via the reaction dNTP→dNMP+PPi. Because of this, the first column utilized in the sequence diagrammed in FIG. 1 is a pyrophosphatase (PPase) column included to remove this contaminating PPi.

In addition to catalyzing the reaction

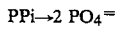

the enzyme system used in the pyrophosphatase column should preferably satisfy the following criteria:
1. no significant APSase activity or activity that significantly alters the concentration of APS;
2. no significant dNTPase activity.

These criteria are met by the enzyme pyrophosphatase as supplied by Sigma Chemical Co., St. Louis, Mo. ("Sigma").

In general, all coupling reactions are carried out in sterile, rubber-stoppered test tubes. Buffer changes are performed by centrifuging briefly and then pipetting off the supernatant. All gels are prewashed in 1 mM HCl before coupling and the enzymes are added to the gel using a 0.2 μm sterile filter.

To prepare the pyrophosphatase column, 10 units of pyrophosphatase is dissolved in 3 ml coupling buffer (0.1M $NaH_2CO_3$, 0.5M NaCl, pH 8.3) and is added to 0.188 g tresyl-activated sepharose 4B. After ethanolamine block, the gel is washed in 10 ml TMN buffer (100 mM TrisOAc, 10 mM $Mg(OAc)_2$, 0.05% $NaN_3$, pH 7.75), suspended in 4 ml TMN buffer containing 2.5 mg/ml $NaN_3$, and stored at 4° C.

The moderate quantity of PPase thus attached to the tresyl-activated sepharose 4B is sufficient for purposes of the present invention. The PPase enzyme is very potent and only small quantities are needed to remove essentially all of the PPi from a sample. Also, employing large quantities of this enzyme on the column may increase the amount of enzyme leakage from the column - leakage which could interfere with the subsequent quantification of PPi.

The PPase column acts as a guard column to insure that the background PPi concentration is reduced to a level of less than about $10^{-12}$M which cannot be measured by the sulfurylase/luciferase method employed to detect PPi. In addition, reduction of PPi is significant to reducing degradation of the growing complementary polymer during wash cycles. It will be understood, however, that the use of this column is optional. Without it, one may elect to pretreat buffers before the procedure to remove any contaminating PPi.

Use of a PPase column limits the choice of buffers used in the feedstock. The buffer that one chooses must not have a large $PO_4^=$ component since PPase catalyzes the reverse reaction as well ($2PO_4^= \rightarrow PPi$). A concentration of 1.0 mM $PO_4$ is enough to cause a sufficient build up of PPi in thermodynamic equilibrium with the $PO_4^=$ to cause a measurable background level of luminescense.

Effluent from the pyrophosphatase column passes into the second column in FIG. 1, the polymerization column. In this column, the template nucleic acid polymer-primer complex and the nucleic acid polymerase are retained. Suitable column materials are positively charged gels such as DEAE-sepharose 6B.

The positively charged gel forms a tight non-covalent bond with the nucleic acid (template+primer) which is a large polyanionic polymer. The polymerase in turn interacts strongly with the binding sight on the nucleic acid located at the 3'-OH primer terminus as the result of its natural affinity. Thus both the nucleic acid to be sequenced and the polymerase enzyme are retained by the column. Neither PPi nor dNTP is significantly retarded by the positively charged gel as used herein.

In order for the method to be successful, the polymerase employed should fulfill the following criteria for purity and enzymatic activity:
1. no significant activity catalyzing dNTP→dNMP+PPi;
2. no significant dNTPase activity;
3. The polymerase preferably should not have significant 3'→5' exonuclease activity. This would correspond to the editing function of polymerase. If the polymerase did hydrolyze the primer strand, the process would rapidly get out of synchronization or perhaps never get started if the primer was completely cleaved. An optimal enzyme for the process though would be an enzyme which has the editing function only if the last nucleotide incorporated is mispaired with the template, and completely devoid of 3'→5' exonuclease activity if the base pairing is correct. Such an enzyme is not, however, presently known. The use of deoxynucleoside [1-thio] triphosphates, which are normally polymerized in the DNA but are resistant to 3'→5' degradation, instead of the use of normal dNTP's, may extend the field of enzymes that can be used successfully.
4. The polymerase should be as accurate as possible. In other words, in the presence of one of the dNTPs, the enzyme must be able to extend the primer chain rapidly only if the base pairing is correct. Further, the polymerase should make a minimal number of miscorporation errors in catalyzing chain extension. The accumulation of errors would also cause the process to lose its synchronization. No enzyme is perfect, but experimental conditions such as optimization of dNTP concentration and pulse time should be employed to minimize such errors.
5. The polymerase must have high processivity. Processivity is defined as the ability of a single enzyme molecule to polymerize nucleotides on a nucleic acid chain without dissociating. This will allow the polymerase to catalyze the incorporation of many nucleotides into the growing primer chain before dissociation of the polymerase from the polymer. This is a necessary property in order to obtain long sequences.

In addition, the polymerase should have no significant PPase activity or other activity which consumes PPi, unless the product of this consumption of PPi is ultimately measured to quantify the amount of PPi produced. Finally, for the sequence of columns depicted in FIG. 1, the polymerase should have no significant APSase activity or activity which consumes APS.

Promising enzymes that appear to meet these criteria are the 180,000 dalton component of calf thymus DNA polymerase type alpha, T7 DNA polymerase which lacks its 3'→5' exonuclease activity, and avian myeloblastosis virus (AMV) reverse transcriptase which is reported to have no 3'→5' exonuclease activity.

A polymerization column for use in the invention can be prepared by introducing a single-stranded template-primer-polymerase complex onto a cationic support material. For small primers which can readily be destroyed by the reverse polymerization reaction, provisions should be taken to prevent this, such as removal of all PPi in the sample before mixing the polymerase with its template-primer substrate and/or inclusion of up to three dNTPs in small concentration, or the development of a synthetic oligonucleotide primer whose 3' terminal base is not susceptible to cleavage in the presence of PPi by replacing the phosphodiester bond with an analogue resistant to nucleophilic attack by PPi.

Template-primer complexes can be prepared by any of the known methods. For example, the template can be primed by adding a nucleic acid fragment that is complementary to a small portion at one end of the polymer to be sequenced, as when the template is cloned in M13 and primed with the M13 universal primer. This method will generally lead to a template whose sequence is partially known since part of the M13 sequence will generally be present between the end of the primer and the start of the unknown sequence.

The next two columns in the method shown in FIG. 1 are kinase columns containing, for example, glycerokinase and hexokinase, respectively. If supplied with appropriate substrates, e.g. glycerol and glucose, these enzymes will selectively degrade contaminating ATP in the mixture into ADP and glycerol phosphate or glucose-6-phosphate. ATP is a common contaminant in commercial preparations of APS (about 0.01%). These enzymes will also cleave dATP to dADP. This is significant since dATP as well as ATP can be utilized by luciferase to generate light.

While glycerokinase and hexokinase are the preferred enzymes for use in the kinase columns, other enzymes can be substituted that meet the following criteria:
1. substantially free of PPase activity, ATP sulfurylase activity, or activity which consumes PPi;
2. substantially free of APSase activity or activity that significantly alters the concentration of APS;
3. must be able to cleave dATP or ATP to dADP and ADP respectively, or to a product which is more inert to luciferase, without generating PPi.

Hexokinase and glycerokinase display the following properties which make them useful. Hexokinase has excellent activity for ATP and its activity for dATP is about half that of ATP. Glycerokinase has good activity for both dATP and ATP. Thus, the enzymes are somewhat complimentary in activity. Neither enzyme has significant kinase activity for the other enzyme substrate. That is, hexokinase cannot use glycerol significantly and glycerokinase cannot use glucose significantly. Thus, the reverse reaction (dADP+glycerol phosphate→dATP+glycerol) does not occur in the hexokinase column to an extent that is measurable or significant. The logic of using the enzymes sequentially as opposed to simply using one column containing a mixture of both hexokinase and glycerokinase is that it gives a thermodynamic advantage. Any dATP or ATP which escapes past the first column is completely removed by the second column. This can also serve as an assurance that ATP and some dATP are removed in the event that one of the columns loses its activity during use.

The activity of the kinases for dTTP, dGTP and dCTP is unimportant if ATP-sulfurylase and luciferase are used as the detection system, as these materials have essentially no utility as substrates for luciferase. If their removal should be significant, however, a method employing nucleoside diphosphate kinase is described below.

While the diagram in FIG. 1 shows the use of two kinase columns, it should be understood that a single functional glycerokinase column works about equally as well. The use of only a hexokinase column does not work as well since some of the dATP will escape cleavage.

In the practice of the invention, hexokinase and glycerokinase are preferably immobilized on a solid support. This can be accomplished as follows: Hexokinase (Sigma H5875), 2000 units, is centrifuged briefly at 13,000 g to remove the $(NH_4)_2SO_4$ supernatant. The pellet is dissolved in 3 ml of coupling buffer, and the hexokinase solution is added to 0.375 g tresyl-activated sepharose 4B. The tube is rotated at room temperature for 2 hours. About 10 ml of 1.0M ethanolamine, pH 8.0, is added to the tube and rotation is continued for 2 hours. The gel is then successively washed in 10 ml coupling buffer, 10 ml of 0.1M NaOAc, 0.5M NaCl, pH 4.0, 10 ml coupling buffer and 10 ml TMN buffer, and then is suspended in 4 ml TMN buffer containing 2.5 mg/ml $NaN_3$ and stored at 4° C. Soluble hexokinase is unstable in coupling buffer, but the short duration of the coupling reaction minimizes the loss of activity.

Glycerokinase from *Bacillus stereothermophilis* (Boerhinger-Mannheim 691-836), 200 μl of the solution, at 500 units/ml is mixed with 2.8 ml of coupling buffer and is added to 0.375 g tresyl-activated sepharose 4B. The Tris contained in the glycerokinase storage buffer does not seem to interfere greatly in the coupling reaction with the protein. The rest of the procedure is identical with the hexokinase procedure.

In the immobilized state, both kinase enzymes show extremely fast kinetics and a great deal of enzymatic activity can be achieved per μl of gel. Both enzymes are inexpensive and can be obtained in large quantities with desired purity. Both enzymes have substrates, glucose and glycerol, which are inexpensive. Both enzymes are stable at room temperature attached to sepharose; neither appear to lose much activity after prolonged use at room temperature or when stored at 4° C. The glycerokinase is able to function well even at 55° C., in soluble form, whereas the hexokinase readily loses activity in soluble form at 60° C. The high catalytic capability/μl gel allows the use of both a short column length and a fast flow rate to minimize the time required to sequence the DNA.

An alternative kinase system employs nucleoside diphosphate kinase (NDK) added to glycerokinase and hexokinase when coupling and ADP added to the buffer solution such that the new columns are (glycerokinase+NDK)-sepharose and (hexokinase+NDK)-sepharose. NDK retains its enzymatic activity when covalently bound to sepharose. This modification of the kinase columns allows for the degradation of all four dNTP's to their respective dNDP's as shown below for (hexokinase+NDK):

The use of only one kinase-NDK-sepharose column is also effective. The major problem with this approach is that commercially available preparations of ADP contain substantial quantities of AtetraP contamination. Because AtetraP is a good substrate for luciferase and cannot be removed enzymatically by either hexokinase or glycerokinase, the ADP preparation probably must be chromatographically purified before use to avoid a large background luminescence.

The use of a kinase column which removes dATP and ATP in the DNA sequencing method is considered optional. In its absence, one need only subtract the additional contribution to background luminescense due to dATP and contaminating ATP in order to compute the quantity of PPi.

The next column depicted in FIG. 1 is an ATP-sulfurylase column. The objective of this column is to convert all the PPi into ATP. Criteria for preferred enzyme purity are listed below:

1. significantly free of PPase activity or activity which consumes PPi other than ATP-sulfurylase;
2. significantly free of nucleoside diphosphate kinase (NDK) or nucleoside monophosphate kinase (NMK) activity;
3. significantly free of hexokinase or glycerokinase activity if glucose or glycerol is included in the buffer respectively;
4. significantly free of any ATPases other than ATP sulfurylase;
5. significantly free of APSase or APS altering activity other than ATP-sulfurylase.

The reasoning behind most of the criteria listed above is self evident in the context of the present invention. As to the absence of NMK activity, if NMK contamination existed, then it would catalyze 2 dNDP→dNMP+dNTP. The dNTP could cause undesirable background luminescense if it is dATP. Another reaction, ATP+dNMP→ADP+dNDP, could consume the ATP formed from the PPi. Similarly, if NDK contamination existed, then it would catalyze ATP+dADP→ADP+dATP; thus, the ATP formed in the ATP-sulfurylase column from PPi would be lost to form dATP which is a poor substrate for luciferase.

A commercially available enzyme preparation that meets these criteria is yeast ATP-sulfurylase (Sigma). This enzyme is stable at room temperature in soluble form or when attached to a gel. The enzyme has a very high catalytic activity and can be attached to tresyl-activated sepharose 4B to yield a high catalytic activity per µl gel.

For example, 50 units of ATP-sulfurylase (Sigma) is dissolved in 1 ml coupling buffer; 950 µl of this solution is heated at 51° C. for 5 minutes, cooled in ice-water 1 minute, diluted with 2 ml coupling buffer and added to 0.188 g of tresyl-activated sepharose 4B. The heating procedure removes most of the hexokinase contamination. The rest of the procedure is identical with the hexokinase procedure.

Because of the high catalytic activity of immobilized ATP-sulfurylase, only a short column length is needed for the flow rates utilized. Also, the high density of enzymatic activity/µl gel allows one to use a smaller excess concentration of APS in the buffers which will still yield complete conversion of PPi to ATP. This reduces the cost of the APS and reduces the background luminescense due to APS.

APS is kinetically a stable molecule. At room temperature only a small loss of APS is measurable over the course of a day. Thermodynamically, however, APS is quite unstable, which contributes to the near irreversibility of its conversion into ATP in the presence of PPi and ATP sulfurylase, with an equilibrium constant in the range of $10^8$. This enzyme is moderately stable at 51° C. for 5 minutes in coupling buffer (loses about 1%–5% activity) and this heating procedure is used to remove the activity of small amounts of contaminating hexokinase.

I have observed a weak side reaction which occurs in the presence of this ATP-sulfurylase preparation, possibly dNTP→dNMP or dNPS+PPi. This side reaction generates small quantities of PPi which is then readily converted to ATP in the presence of APS. It is unknown whether this activity is due to a contaminating enzyme or due to the ATP-sulfurylase itself. The order of reactivity is dTTP>dGTP>dCTP. The use of low concentrations of dNTP ($<10^{-5}$M) is effective in eliminating most of this additional source of background luminescense. An alternative solution is to use the NDK-kinase columns described earlier so that all four dNTP's are converted to their dNDP form which is unable to participate in the reaction above.

The final column depicted in FIG. 1 is a luciferase column which contains an ATP-dependent luciferase to catalyze the reaction:

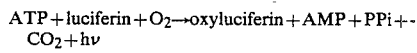

The enzyme preparation used in the luciferase column should preferably satisfy the following criteria:
1. significantly free of NMK or NDK activity;
2. significantly free of hexokinase and glycerokinase activity if glucose or glycerol is included in the buffer, respectively;
3. significantly free of ATPases other than luciferase and ATP-sulfurylase.

Enzyme preparations are readily and inexpensively available which satisfy the above criteria. In addition, it is advantageous that the solid support material chosen for attachment is significantly able to transmit light. One type of material that satisfies this is sepharose 4B.

Luciferase can be coupled to tresyl-activated sepharose 4B using two different methods.

METHOD (A)—Tresyl-activated sepharose 4B is washed four times with 10 ml 1 mM HCL. Luciferase dissolved in coupling buffer is added to the sepharose through a 0.2 µm sterile filter. The mixture is rotated at room temperature for 2 hours at 30 rpm. About 10 ml of 1.0M ethanolamine, pH 8.0, is then added and the mixture is rotated for an additional 2 hours. The sepharose is then successively washed in 10 ml coupling buffer, 10 ml of 0.1M NaOAc, 0.5M NaCl, pH 4.0, and 10 ml TMN buffer, and suspended in 4 ml TMN buffer+2.5 mg/ml NaN$_3$ for storage at 4° C. This method was modified in Method B to allow for more protein coupling to occur.

METHOD (B)—Tresyl-activated sepharose 4B is washed 3 times with 10 ml 1 mM HCL. Luciferase is dissolved in 50 mM NaH$_2$PO$_4$, 10 mM NaCl, pH 7.75 containing 25% glycerol (luciferase buffer) and is added to the washed gel using a 0.2 µm sterile filter. The mixture is rotated at about 2 rpm at room temperature for 9 hours. Then NaN$_3$ is added to about 2.5 mg/ml for storage at 4° C.

An additional enzyme column not shown in FIG. 1 may advantageously be incorporated between the sulfurylase column and the luciferase column to remove unreacted APS, since APS can act as a substrate for luciferase.

The attached enzyme in this column should fulfill several criteria:
1. significantly free of NDK or NMK activity;
2. significantly free of hexokinase or glycerokinase activity if glucose or glycerol is included in the buffer respectively;
3. significantly free of ATPases;
4. must be able to convert APS into a product which does not interact significantly with luciferase to form The purpose of this column is to eliminate the background luminescence resulting from the weak reaction of APS with luciferin. This is achieved by converting or cleaving the APS to a product which does not react with luciferin/luciferase. Note that according to the criteria listed the enzyme must selectively cleave APS without acting on ATP. There are several types of enzymes reported in the literature which may fulfill these criteria. The first is an APS-sulfatase which catalyzes the reaction APS→AMP+SO$_4$=. Many organisms contain an enzyme with this activity. One such enzyme has been isolated from *Anabaena cylindrica,* Sawhney et al., 6 *Plant Sci. Lett.* 103 (1976). Another type of enzyme which may accomplish the job is ADP-sulfurylase which catalyzes the reaction APS+PO$_4$=→ADP+SO$_4$=. There are two different enzymes which have been isolated from yeast with this activity. The equilibrium for both of these reactions is far to the right and both products, AMP and ADP, have virtually no ability to excite luciferin/luciferase. Other enzymes that may be suitable catalyze the reactions APS→cAMP+SO$_4$= or APS+NH$_3$→adenosine-5'-phosphoramidate +SO$_4$=. Enzymes with these activities have been isolated from *Chlamydomonas reinhardtii* and *Chlorella pyrenoidosa,* respectively. The activities of some of these enzymes for ATP have not been fully investigated.

The use of this enzyme column is considered optional, that is, a sequence can be determined without using it, but it is necessary to subtract the background luminescense due to APS. By eliminating the background luminescense due to APS, the addition of this enzyme to the process will allow more precise quantitation of very low concentrations of PPi (down to about 10$^{-12}$M). If APSase is not used it may be possible to combine ATP-sulfurylase and luciferase in one column.

Other modifications to the columns used in the sequencer might also be made without departing from the spirit and scope of the invention. For example, one problem that has been noted is degradation of the growing complementary polymer during the wash cycle as a result of PPi contamination. This problem might be reduced by introducing further columns before the polymerization column to more thoroughly remove the PPi. Thus, a column containing ATP-sulfurylase or some other PPi-consuming enzyme with a large equilibrium constant might be incorporated in place of or in addition to the PPase column.

Another approach to reducing the effect of PPi contamination would involve placing a PPi utilizing enzyme within the polymerization column itself. Of course, such an enzyme could not be a pyrophosphatase, but rather would have to produce a measurable product. For example, ATP-sulfurylase might be incorporated in the polymerization column, so long as any kinase columns downstream of the polymerization column were omitted.

Once the various enzymes are coupled to appropriate supports, columns for use in the method are prepared. For each immobilized enzyme, a small capillary tube (1.1 mm ID, 1.5 mm OD) is plugged at one end using glass wool. Using sterile syringes, concentrated NaOH is washed through the column to sterilize it. This is followed by a wash of sterile water, then sterile buffer. The enzyme-sepharose 4B gel is then loaded into the column to the specified height. The glass tube is then cut several millimeters above the top of the sepharose. The capillary columns are then connected in the order shown in FIG. 1 using silicon tubing (0.04" ID, 0.085" OD) or some similar connection means. All tubing used is precleaned in the sam manner as the capillary tubes before use. Between use, the columns are stored in TMN buffer plus 25% glycerol and 2.5 mg/ml NaN$_3$ at 4° C.

For use, the luciferase column is placed within a detector means for quantifying the amount of light produced. For example, the luciferase column can be placed within a cell such as that shown in FIG. 2 and then in the sample compartment of an LB9500C luminometer (Berthold).

After the columns have been assembled into an apparatus for sequencing nucleic acids, and the template-primer-polymerase complex has been placed in the polymerization column, a series of feedstocks is introduced into the apparatus, each feedstock containing one nucleotide, APS, luciferin and a substrate for the kinase column(s), if present.

To illustrate the logic of the method, let us assume that we wish to sequence the template-primer complex shown below:

5' primer - A-T-G-A

3' template - T-A-C-T-C-T-T-A-G-C-C-G-A-A-A 5'

Assume also that we select the following order of dNTP's:

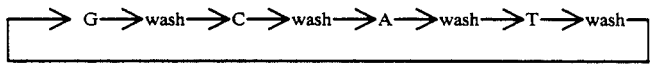

Figure 3:
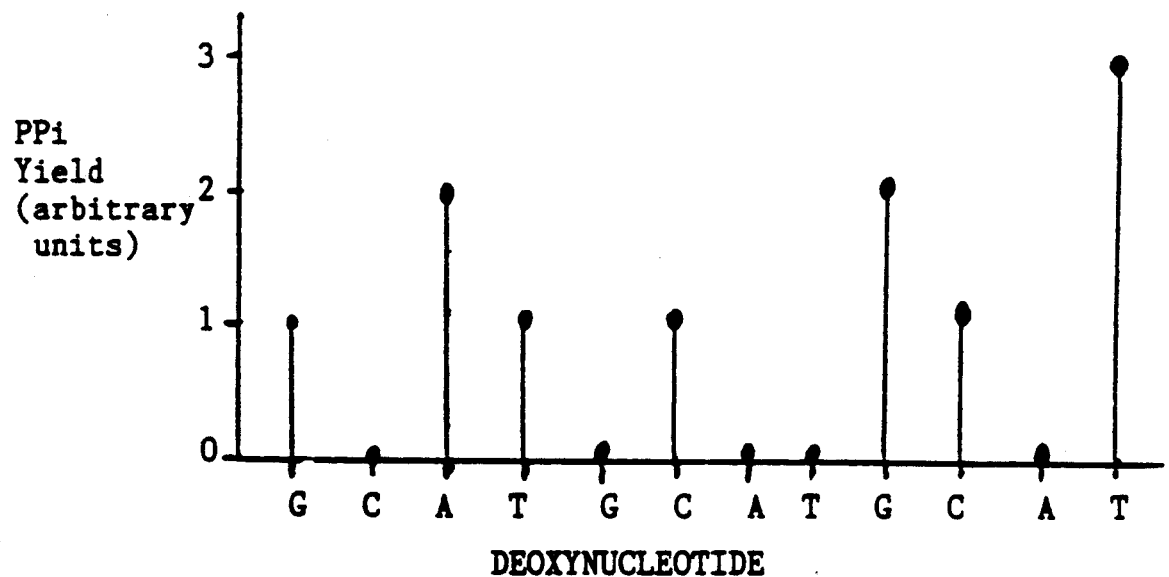
FIG. 3 shows the predicted light output observed during sequencing of a theoretical template polymer.

We would thus obtain the result shown in FIG. 3 which plots PPi quantitated vs. nucleotide. This plot of PPi vs. dNTP readily tells us that the polymerized sequence is GAATCGGCTTT and thus allows determination of the complimentary template sequence.

Figure 6:
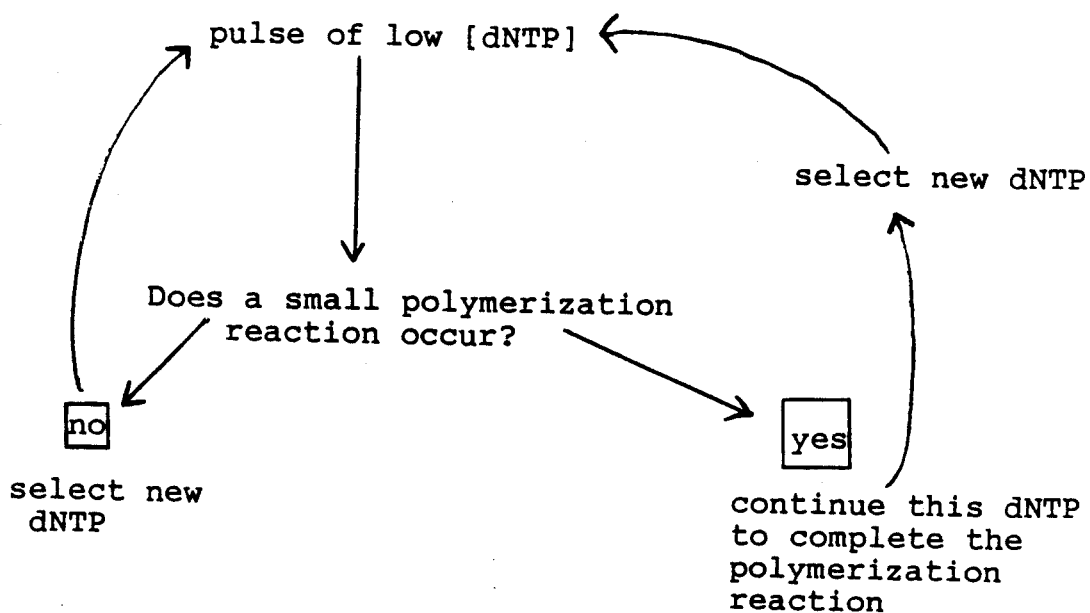
FIG. 6 shows a logical flow path for the introduction of feedstocks to a sequencer according to the invention.

The introduction of dNTP feedstocks can follow a regular sequence, e.g. the GCAT sequence depicted above, or it can be controlled in some other manner. For example, it might be desirable to control the feedstock input based upon the light being produced. In this case, a dNTP feedstock flow would be introduced for a specified minimum time to determine if reaction was occurring. If polymerization occurred, the flow of feedstock would then be maintained or perhaps increased, or the concentration of dNTP increased, until light output, as an indicator of polymerization, essentially stopped. The next feedstock would then be introduced. The logic of such a control scheme is shown in FIG. 6.

The selection of the new dNTP which occurs either following completion of polymerization or in the absence of polymerization can follow any of several logics. For example, the feedstocks could be introduced in a fixed order regardless of whether reaction has occurred or not. Alternatively, the cycle could be reset following every second nucleotide incorporation in view of other known data such as the percentages of various bases. For example, if a given sequence is known to be GC rich, it would be reasonable to test each successive base in the template for G and C base pairing before testing for A and T. Finally, when dealing with a portion of the template for which the sequence is already known, e.g., a part of a cloning vector, the feedstocks can be introduced in this sequence, or even as mixtures of up to three bases at a time.

EXAMPLE

As a simple illustration of the DNA sequencing protocol, the synthetic alternating copolymer poly(dAdT) was sequenced using AMV reverse transcriptase. DNA-DNA polymerase-DEAE sepharose 6B was prepared by dissolving 0.26 units of poly(dAdT) in 10 µl of 10 mM Tris-HCl, 5 mM NaCl, pH 7.5 and adding this to 20 µl of sequencing buffer (25 mM TrisOAc, 10 mM Mg(OAc)$_2$, 1 mM dithioerythritol, 0.05% NaN$_3$, 10 mM glucose, 10 mM glycerol, $5 \times 10^{-7}$M APS pH 7.75). No primer was necessary in this case, because poly(dAdT) is self-priming. 50 units of AMV reverse transcriptase were then added and the mixture was incubated at room temperature for about 1 minute. The incubated mixture was then diluted with 500 µl of sequencing buffer, and injected through a 10 mm DEAE sepharose 6B column, pre-equilibrated in sequencing buffer. The polymerase column was then placed in a sequencer formed from a PPase column, 15 mm gel height; a glycerokinase column, 40mm; a hexokinase column, 20 mm; an ATP sulfurylase column, 15 mm; and a luciferase column, 10 mm. The luciferase column was prepared from 0.190 g gel+0.4 mg firefly luciferase (Sigma L9009) in 3 ml buffer (50 mM NaH$_2$PO$_4$, 10 mM NaCl, pH 7.75, 25% glycerol) using method B.

Figure 2:
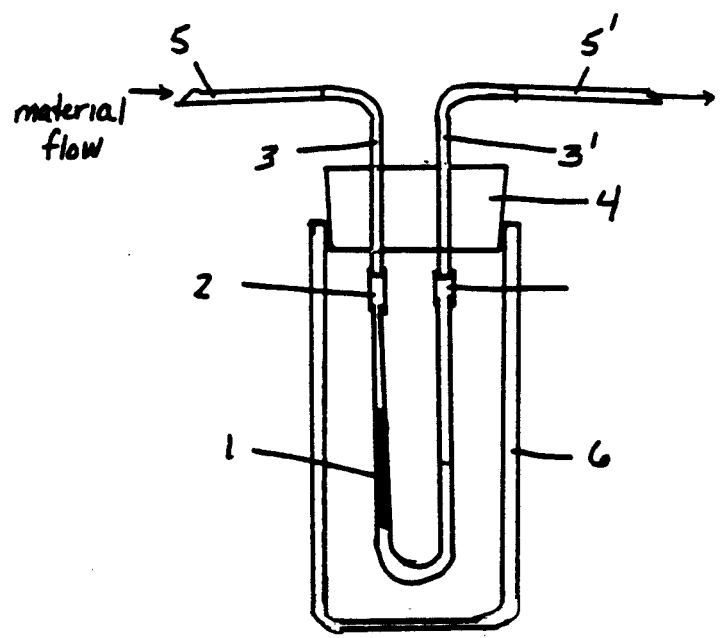
FIG. 2 shows a cell construction suitable for use in measuring luminescence from the luciferase column.

The luciferase column was placed within a flow-cell of the type depicted in FIG. 2. In this cell, the ends of the luciferase column 1 were connected via silicon tubing 2 and 2' to two 18 gauge stainless steel needles 3 and 3'. The needles 3 and 3' passed through a partially hollowed black rubber stopper 4 and then connected to tubing 5 through which a flow material from the preceding columns is delivered to the luciferase column and tubing 5' which carries the effluent from the luciferase column to a waste reservoir. The luciferase column 1 was placed within a cuvette 6 for the LB9500C luminometer which was sealed in the counting chamber by the rubber stopper 4. The needles 3 and 3' were bent to block entry of external light through the needle bores into the cuvette 6.

After equilibrating the sequencer with sequencing buffer, dNTP feedstocks ($10^{-7}$M in sequencing buffer) were used in 1 minute pulses immediately followed by a 12 minute wash with sequencing buffer; flow rate=75 µl/min.

Figure 4:
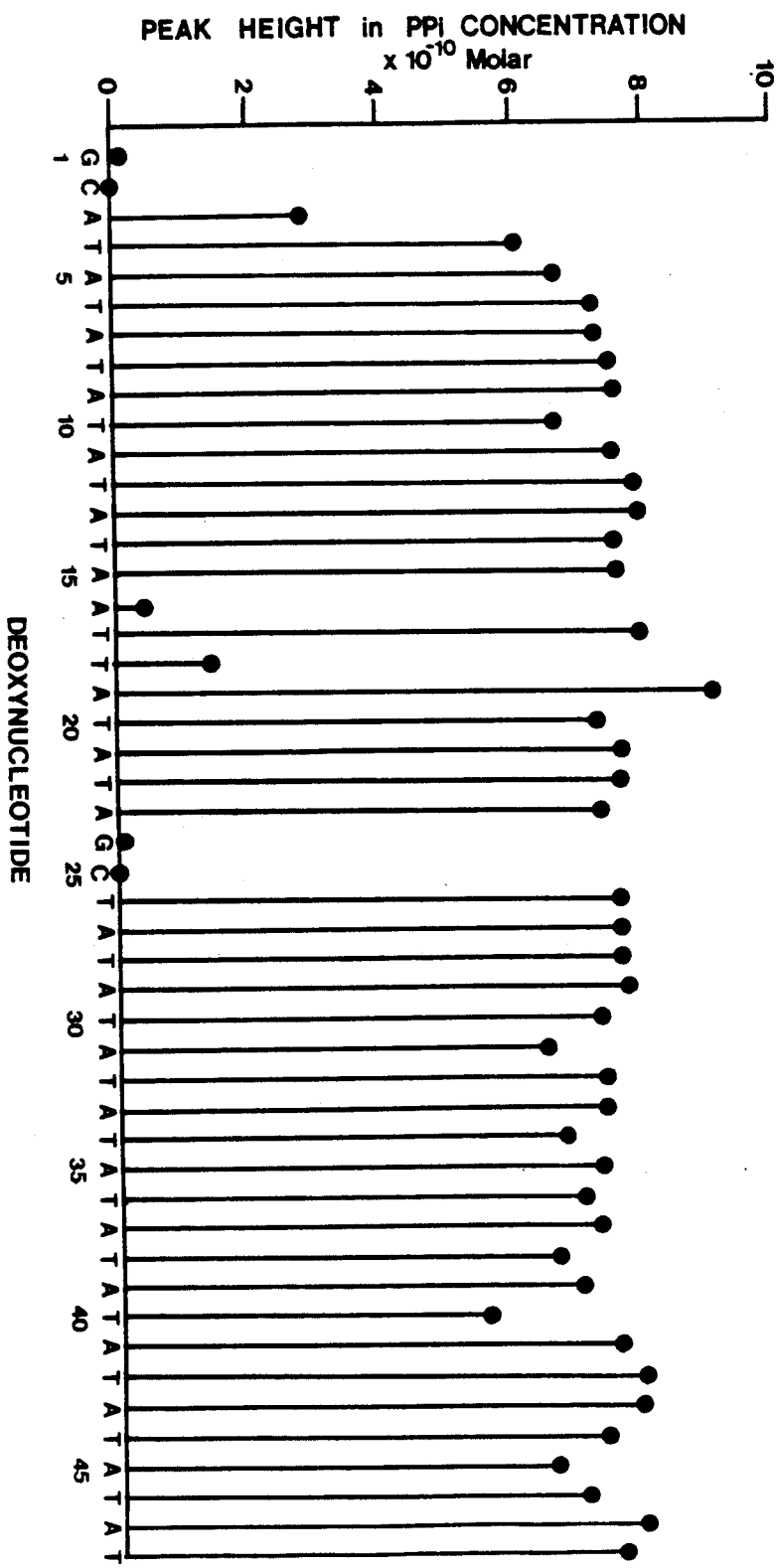
FIG. 4 shows the peak heights observed during sequencing of a synthetic poly dAdT polymer.

The observed luminescence is shown in FIG. 4. After the initial three pulses of dNTP feedstock, large peaks were observed so long as dATP and dTTP feedstocks were provided alternately. The sequence determined is obviously poly(dAdT) from the figure. Several other features of the data in FIG. 4 are also worthy of comment.

The first pulse of dATP gave only about one half the PPi yield. This is probably due to the random cleavage of the primer strand by reverse polymerization which occurred during sample preparation so that the next nucleotide required for half the templates is dATP and the other half is dTTP. The first pulse of dATP returns the system to synchronization since the next nucleotide required by all templates is now dTTP.

A pulse of dATP immediately following a pulse of dATP gave only small areas of reaction. This is expected since the reaction with the first pulse goes to almost full completion and the next nucleotide required is dTTP. The small response in pulse 16 of dATP appears to have three causes: (1) misincorporation of dATP in place of dTTP (minor); (2) degradation of the primer strand during the wash cycle due to PPi contamination in the column (major); and (3) incomplete polymerization during the preceding pulse 15 (major). A similar result is observed with consecutive pulses of dTTP.

dGTP and dCTP give practically no polymerization, as expected, since neither can base pair properly with the growing DNA chain. This shows that at the dNTP concentration of $10^{-7}$M, AMV reverse transcriptase makes few "mistakes."

The length of the sequence determined was about 42 base pairs. The yield of PPi measured due to polymerization, about $9.4 \times 10^{-14}$ moles, decreases only slightly during the sequence. This is attributed to the high processivity of the enzyme AMV reverse transcriptase. AMV reverse transcriptase incorporates an average of several hundred nucleotides before dissociating. When an enzyme with low processivity like the Klenow fragment was used, the yield of PPi obtained after each chain extension decreased much faster until all of the polymerase was washed off of the gel. The sequence determined above could have been longer, but the experiment required about 12 hours to complete, and was discontinued due to time constraints. The use of other solid supports such as silica gel or alumina may allow faster flow rates and thus, faster sequencing.

The foregoing example demonstrates that the method of the invention is operative. It does not, however, address the potential problem of losing synchronization as a result of the accumulation of errors and incomplete polymerization reactions, because this problem is not of particular significance for poly(dAdT). If a particular base pair does not form when it should, it will simply form with the next pulse of the appropriate nucleotide. In the case of a sequence determination for a real nucleic acid polymer, however, loss of synchronization could present a problem. Accordingly, care should be taken to allow exposure to each feedstock under conditions such that substantially complete chain lengthening has occurred and few errors are made.

Lack of synchronization might also occur as a result of the presence of primer strands of different lengths for reasons other than incomplete polymerization. Chain terminating nucleotides like dideoxynucleotides (ddNTP) may also be useful in eliminating background noise caused by this problem. For example, if it is determined using a pulse at very low dATP concentration that the next nucleotide in the sequence will be A, one can then give a pulse of a mixture of ddGTP, ddCTP, and ddTTP to terminate primer chains that are the wrong length prior to adding sufficient dATP to complete the polymerization.

Figure 5:
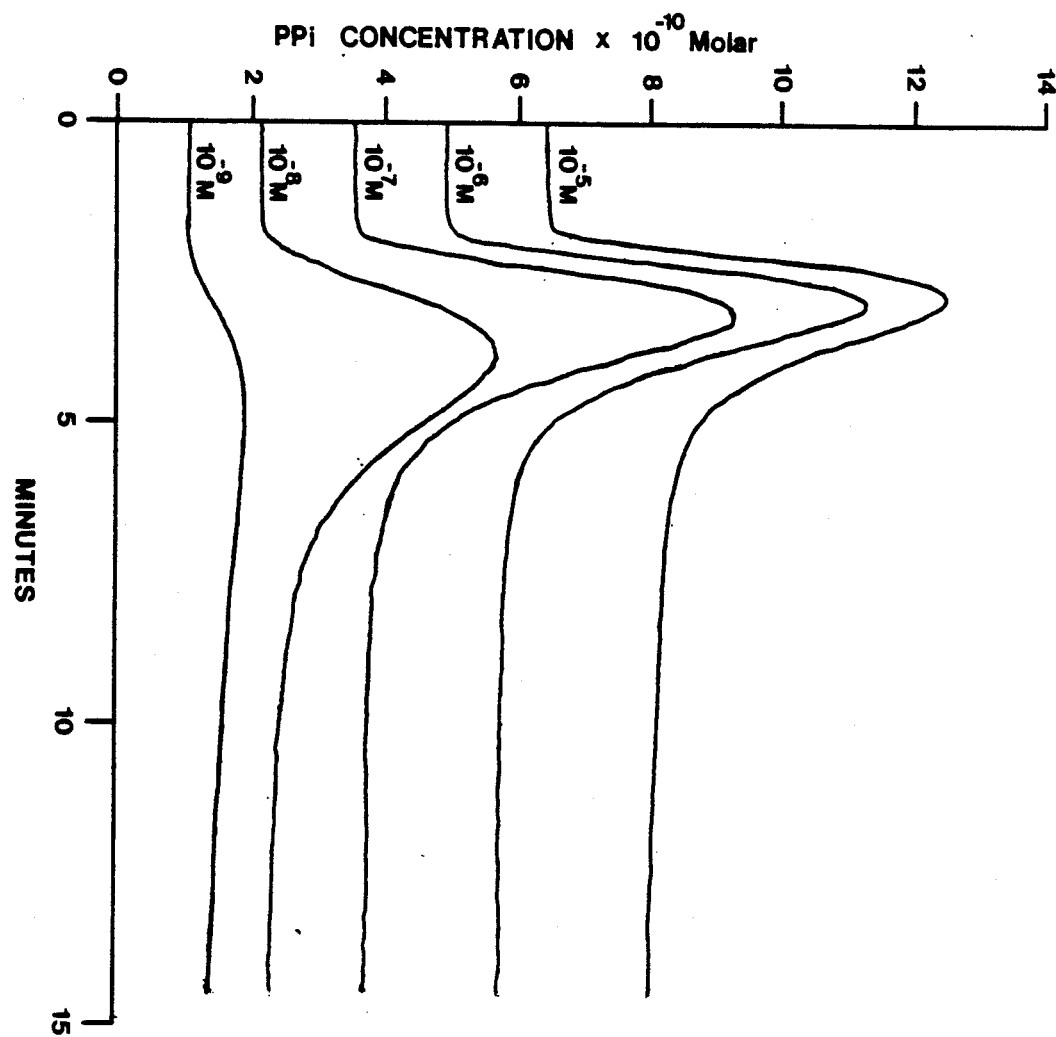
FIG. 5 shows luminescence output for continuous dATP pulses at various concentrations.

As a general rule, complete reaction can be insured by lengthening the exposure time or by increasing the concentration of dNTP in the feedstock. However, both can lead to increased polymerization errors and optimal dNTP concentration and pulse times may differ for different polymerases. The frequency of polymerization errors for AMV reverse transcriptase as a function of the concentration of dATP is examined in detail in FIG. 5. The peaks were obtained by a continuous flow of dATP at different concentrations of dATP. All peaks were obtained after a 1 minute pulse with $10^{-7}$M dTTP followed by a 1 ml wash. This insures synchronization of the sequence of the sequence so that dATP is the next nucleotide required in the sequence.

At $10^{-9}$M dATP the polymerization reaction occurs so slowly that one does not obtain an initial peak, but a broad slowly declining plateau instead. The ability of dATP to be polymerized at such low concentrations emphasizes the need to fully wash a dNTP out of the polymerization column before introducing the next feedstock. At $10^{-8}$M the peak observed is broad due to slow polymerization, with a slow decline of rate back to baseline level. The error rate observed here is approximately zero. At $10^{-7}$M the peak obtained is much sharper, somewhat similar to the peak obtained using a 1 minute pulse of $10^{-7}$M dATP. The decline from the peak, however, never returns to baseline level. I postulate that this is due to a low frequency event in which dATP is mistakenly polymerized in the DNA in place of dTTP. Similarly, at $10^{-6}$M and $10^{-5}$M the light output does not return to baseline. Moreover, the gap between the residual light intensity and the baseline is much larger here indicating a higher rate of error making. This corresponds to what is intuitively obvious, i.e., the larger the dATP concentration, the faster the polymerase will make errors. The estimated frequency of error production for $10^{-5}$M and $10^{-6}$M dATP are 7.7%/min. and 3.8%/min., respectively. These values have been corrected to take into account the fact that after an error is produced, it will be followed by a fast polymerization of another molecule of dATP which can base pair correctly. The relationship of error rate vs. dNTP concentration holds true for the other dNTPs as well, e.g., increasing concentrations of dGTP result in increasing incorporation of dGTP into the poly(-dAdT).

Based upon these observations, it appears that feedstocks for use in the invention will advantageously contain nucleotide at a concentration of about $10^{-7}$M when using AMV reverse transcriptase. In addition, the feedstocks will contain APS, and luciferin and a substrate for the kinase column(s). The concentration of APS should also be maintained at a low level, because of the fact that APS can serve as a weak alternate substrate of luciferase to produce light. One can compute an equivalent concentration of ATP that would give the same rate of luminescense produce APS by the formula below:

$$[ATP]\text{ equivalent} = 2.4 \times 10^{-4} [APS]$$

The background luminescense of APS can be minimized by utilizing as small a concentration of APS as possible while still allowing for complete conversion of the PPi to ATP. At flow rates used experimentally it was observed that $5 \times 10^{-7}$M APS is adequate for measuring a concentration of $2 \times 10^{-8}$M PPi. The small excess of APS can be used due to the high density of enzymatic activity of ATP sulfurylase/$\mu$l of gel and the fast kinetics of the reaction.

I claim:

1. A method for determining the nucleic acid sequence in a template nucleic acid polymer, comprising
    (a) introducing the template nucleic acid polymer into a polymerization environment in which the nucleic acid polymer will act as a template polymer for the synthesis of a complementary nucleic acid polymer when nucleotides are added;
    (b) successively providing to the polymerization environment a series of feedstocks, each feedstock comprising a nucleotide selected from among the nucleotides from which the complementary nucleic acid polymer will be formed, such that if the nucleotide in the feedstock is complementary to the next nucleotide in the template polymer to be sequenced said nucleotide will be incorporated into the complementary polymer and inorganic pyrophosphate will be released;
    (c) separately recovering each of the feedstocks from the polymerization environment; and
    (d) measuring the amount of inorganic pyrophosphate in each of the recovered feedstocks to determine the identity of each nucleotide in the complementary polymer and thus the sequence of the template polymer.

2. A method according to claim 1, wherein the amount of inorganic pyrophosphate is measured by
    adding adenosine-5'-phosphosulfate to the feedstock;
    combining the recovered feedstock containing the adenosine-5'-phosphosulfate with the enzyme ATP-sulfurylase such that any inorganic pyrophosphate in the recovered feedstock and the adenosine-5'-phosphosulfate will react to the form ATP and sulfate;
    combining the ATP and sulfate-containing feedstock with luciferin and an ATP-dependent luciferase in the presence of oxygen such that the ATP is consumed to produce AMP, inorganic pyrophosphate, carbon dioxide and light; and
    measuring the amount of light produced.

3. A method according to claim 1, wherein the template polymer is immobilized on a solid support.

4. A method according to claim 3, wherein the immobilized template polymer is complexed with a primer sequence.

5. A method according to claim 4, wherein the template-primer complex is bound to a nucleic acid polymerase.

6. A method according to claim 5, wherein the amount of inorganic pyrophosphate is measured by
    adding adenosine-5'-phosphosulfate to the feedstock;
    combining the recovered feedstock containing the adenosine-5'-phosphosulfate with the enzyme ATP sulfurylase such that any inorganic pyrophosphate in the recovered feedstock and the adenosine-5'-phosphosulfate will react to form ATP and sulfate;
    combining the ATP and sulfate containing feedstock with luciferin and an ATP-dependent luciferase in the presence of oxygen such that the ATP is consumed to produce AMP, inorganic pyrophosphate, carbon dioxide and light; and measuring the amount of light produced.

7. A method according to claim 1, wherein each feedstock comprises adenosine-5'-phosphosulfate and luciferin in addition to the selected nucleotide base, and the amount of inorganic pyrophosphate is determined by reacting the inorganic pyrophosphate-containing feedstock with ATP sulfurylase and then with an ATP-dependent luciferase thereby producing light in an amount proportional to the amount of inorganic pyrophosphate, and measuring the amount of light produced.

8. A method according to claim 7, further comprising the step of treating the feedstock to remove inorganic pyrophosphate prior to providing the feedstock to the polymerization environment.

9. A method according to claim 8, wherein the feedstock is treated with immobilized pyrophosphatase enzyme to remove inorganic pyrophosphate prior to providing the feedstock to the polymerization environment.

10. A method according to claim 7, further comprising the step of treating the feedstock to remove ATP prior to reacting the feedstock with the ATP sulfurylase.

11. A method according to claim 10, wherein the feedstock further comprises glycerol and wherein the feedstock is treated with glycerokinase to remove ATP.

12. A method according to claim 10, wherein the feedstock further comprises glucose and wherein the feedstock is treated with hexokinase to remove ATP.

13. A method according to claim 11, wherein the feedstock further comprises glucose and wherein the feedstock is treated with hexakinase to remove ATP.

* * * * *